(12) United States Patent
Kassab et al.

(10) Patent No.: US 10,390,713 B2
(45) Date of Patent: Aug. 27, 2019

(54) METHODS FOR THE NON-INVASIVE DETERMINATION OF HEART AND PULMONARY PRESSURES (71) Applicants: Ghassan S. Kassab, Zionsville, IN (US); Yunlong Huo, Beijing (CN)

(72) Inventors: Ghassan S. Kassab, Zionsville, IN (US); Yunlong Huo, Beijing (CN)

(*) Notice: Subject to any disclaimer, the term of this patent is extended or adjusted under 35 U.S.C. 154(b) by 982 days.

(21) Appl. No.: 14/215,027

(22) Filed: Mar. 16, 2014

(65) Prior Publication Data
US 2014/0275961 A1 Sep. 18, 2014

Related U.S. Application Data (60) Provisional application No. 61/788,399, filed on Mar. 15, 2013.

(51) Int. Cl.
A61B 6/00 (2006.01)
G06T 7/00 (2017.01)
(Continued)

(52) U.S. Cl.
CPC ........ *A61B 5/02133* (2013.01); *A61B 5/0263* (2013.01); *A61B 5/055* (2013.01); *A61B 6/503* (2013.01); *A61B 6/504* (2013.01); *A61B 8/04* (2013.01); *A61B 8/06* (2013.01); *A61B 8/485* (2013.01); *A61B 8/5223* (2013.01); *G06T 7/0012* (2013.01); *G16H 50/30* (2018.01); A61B 5/022 (2013.01); A61B 5/0265 (2013.01); A61B 8/0883 (2013.01); G01R 33/20 (2013.01)

(58) Field of Classification Search
CPC ... A61B 5/02133; A61B 5/022; A61B 5/0263; A61B 5/0265; A61B 5/055; A61B 8/04; A61B 8/06; A61B 8/0883; A61B 8/485; A61B 8/5223; A61B 6/504; A61B 6/503; G16H 50/30; G06T 7/0012; G01R 33/20
See application file for complete search history.

(56) References Cited

U.S. PATENT DOCUMENTS 5,178,151 A * 1/1993 Sackner ............... A61B 5/7239
600/485
2002/0151805 A1* 10/2002 Sugo .................. A61B 5/02125
600/504
(Continued)

OTHER PUBLICATIONS

Ge et al. "Noninvasive evaluation of right ventricular and pulmonary artery systolic pressures in patients with ventricular septal defects: simultaneous study of Doppler and catheterization data." Am Heart J. Apr. 1993;125(4):1073-81.*

*Primary Examiner* — Amanda Lauritzen Moher
(74) *Attorney, Agent, or Firm* — Reichel Stohry LLP; Mark C. Reichel; Natalie J. Dean (57) ABSTRACT The disclosure of the present application provides methods for the noninvasive determination of cardiac and pulmonary pressures based off of patient-specific medical images and one or more computations. In one exemplary embodiment, the method comprises noninvasively generating a patient-specific medical image of at least a portion of a heart, determining a free vibration measurement from the left ventricular free wall based on the patient-specific image, and performing at least one computation using the free vibration measurement to noninvasively determine a cardiac or pulmonary pressure.

14 Claims, 3 Drawing Sheets (51) Int. Cl.
*A61B 5/021* (2006.01)
*A61B 8/04* (2006.01)
*G16H 50/30* (2018.01)
*A61B 5/026* (2006.01)
*A61B 5/055* (2006.01)
*A61B 8/06* (2006.01)
*A61B 8/08* (2006.01)
*G01R 33/20* (2006.01)
*A61B 5/022* (2006.01)
*A61B 5/0265* (2006.01)

(56) References Cited

U.S. PATENT DOCUMENTS

| | | | | |
|---|---|---|---|---|
| 2003/0195409 | A1* | 10/2003 | Seitz | A61B 5/0205 600/407 |
| 2011/0144967 | A1* | 6/2011 | Adirovich | G06F 19/3406 703/11 |
| 2012/0041318 | A1* | 2/2012 | Taylor | A61B 5/02007 600/504 |
| 2012/0243758 | A1* | 9/2012 | Otani | A61B 8/08 382/131 |
| 2012/0296209 | A1* | 11/2012 | Tanaka | A61B 8/0883 600/438 |
| 2013/0226003 | A1* | 8/2013 | Edic | A61B 6/504 600/454 |

\* cited by examiner

METHODS FOR THE NON-INVASIVE DETERMINATION OF HEART AND PULMONARY PRESSURES

PRIORITY CLAIM

This application is related to and claims the priority benefit of U.S. Provisional Patent Application Ser. No. 61/788,399 to Kassab et al., filed Mar. 15, 2013. The contents of the aforementioned application is hereby incorporated by reference in their entirety into this disclosure.

BACKGROUND

Measurements of heart and pulmonary pressures are very significant for diagnosis of systolic and diastolic heart failures, ventricular infarction, and other heart conditions. Specifically, such pressures are directly related to the mechanical properties of the cardiac muscle and, as such, different parameters of the cardiac cycle can be used to determine the status of a patient's heart function and/or to diagnose specific heart-related conditions.

Conventional monitoring and measuring techniques are typically invasive, often requiring sensors or other measurement devices to be placed within the heart or the vessels connected thereto. Such invasive measurements are costly, time-consuming and potentially dangerous to the patient. For example, conventional methods dictate catheterizing the left ventricle of the heart to obtain a direct measurement of left ventricular end-diastolic pressure (LVEDP). However, catheterizing the left ventricle is both highly invasive and risky, as it is associated with serious complications including stroke and death. Accordingly, the conventional invasive techniques used to obtain direct pressure measurements from a heart are undesirable as routine diagnostic tests and are impractical in a non-clinical setting.

While some techniques exist for non-invasively measuring heart and pulmonary pressures during the cardiac cycle, such techniques are limited and, in some cases, only approximate the desired measurements. For example, in the absence of aortic valve disease, left ventricle (LV) systolic pressure ($P_{LVSP}$) equals the synchronous aortic pressure (i.e., $P_{LVSP}=P_{AP}$) and can therefore be accurately determined noninvasively. However, the non-invasive estimation of LVEDP, right ventricle (RV) pressure, and pulmonary pressure is currently a great challenge using conventional techniques. The LVEDP is empirically estimated from pulmonary venous and mitral flows, which lacks a theoretical basis and, at best, provides only an approximation of the targeted pressure. Furthermore, the non-invasive method for assessing RV and pulmonary pressures is to add the transtricuspid pressure gradient (computed by a modified Bernoulli equation based on the maximum velocity of the regurgitant jet) to the mean right atrial pressure (estimated clinically from the jugular veins). It is difficult, however, to non-invasively measure jugular vein pressure and to accurately compute the transtricuspid pressure gradient using a modified Bernoulli equation in patients. Hence, there exists a clear clinical need for improved methods for the non-invasive determination of LVEDP, RV and pulmonary pressures, based on laws of mechanics and not simply empirical data.

BRIEF SUMMARY

In at least one exemplary embodiment of a method for noninvasively determining a pressure of the present disclosure, the method comprises generating a patient-specific medical image of at least one portion of a heart of a patient noninvasively; determining at least one measurement from a portion of the heart in the patient-specific medical image; and performing one or more computations using the measurement to noninvasively determine at least one targeted pressure within one or more portions of the heart and/or an adjacent vessel. The at least one targeted pressure may be selected from the group consisting of a left ventricle (LV) end-diastolic pressure (LVEDP), a right ventricle (RV) pressure, and a pulmonary pressure. The patient-specific medical image may be generated through magnetic resonance imaging, echocardiography or any other noninvasive imaging technology. Furthermore, in at least one embodiment, the at least one measurement comprises a free vibration measurement. Where such free vibration measurement may be obtained from a free wall of a LV of the heart, at least one of the computations may determine end-diastolic Young's modulus of LV wall using the free vibration measurement. In yet another embodiment, at least one of the computations determines patient-specific material parameters in diastolic strain energy function (SEF) through numerical optimization (inverse method) such that Young's modulus from SEF is substantially equal to the value of the end-diastolic Young's modulus of the LV free wall determined from the free vibration measurement. In an additional embodiment, the at least one measurement determined from the patient-specific medical image relates to the position of the left ventricular free wall, the at least one targeted pressure comprises a LVEDP, and at least one of the computations determines the LVEDP by iterative solution such that a predicted LV free wall position substantially matches the at least one measurement related to the position of the LV free wall. Furthermore, the at least one measurement determined from the patient-specific medical image may relate to the position of an interventricular septum, and at least one of the computations determines RVEDP end by iterative solution such that a predicted end-diastolic interventricular septum position substantially matches the at least one measurement related to the position of the interventricular septum.

In yet another embodiment of an exemplary method of the present disclosure, the method further comprises the step of determining LVSP by noninvasively measuring aortic pressure; LVSP being substantially equivalent to aortic pressure. Additionally, at least one of the measurements determined from the patient-specific medical image may relate to the position of the LV systolic free wall. In such embodiment, one of the targeted pressures may comprise RVSP systolic pressure and at least one of the computations may calculate patient-specific material parameters of the heart in systolic second Piola-Kirchhoff stress by numerical optimization (inverse method) such that a predicted LV systolic free wall position substantially matches the measurements related to the position of the LV systolic free wall. Additionally or alternatively, at least one of the measurements determined from the patient-specific medical image may relate to the position of a systolic interventricular septum. There, a targeted pressure may comprise RVSP and at least one of the computations is for calculating right ventricular systolic pressure by iterative solution such that a predicted systolic interventricular septum position substantially matches the measurements related to the position of the systolic interventricular septum. In addition to the aforementioned, in at least one embodiment, the method further comprises the step of calculating a blood flow velocity and determining a pressure gradient from the blood flow velocity, wherein at least one of the targeted pressures comprises pulmonary pressure derived from the right ventricular systolic pressure and the pressure gradient. Such pressure gradient may be determined from magnetic resonance imaging blood flow velocity measurements through a right ventricle of the heart. In yet another embodiment, the method may further comprise the steps of noninvasively determining venous pressure; and using the venous pressure as reference for determining and/or validating the pressure gradient.

Still further, embodiments of the method may comprise the steps of determining a pressure gradient based on blood flow velocity measurements obtained from the patient-specific medical image; determining left ventricular systolic pressure by noninvasively measuring aortic pressure, left ventricular systolic pressure being substantially equivalent to aortic pressure; and assessing the pressure difference across an interventricular septum in view of the left ventricular systolic pressure to determine right ventricular systolic pressure.

Methods for noninvasively determining RVSP are also disclosed. Embodiments of such methods may comprise the steps of determining a pressure gradient based on blood flow velocity measurements through the right ventricle of a heart; determining left ventricular systolic pressure by noninvasively measuring aortic pressure; and assessing the pressure difference across an interventricular septum in view of the left ventricular systolic pressure to determine right ventricular systolic pressure. Furthermore, such methods may additionally comprise the steps of noninvasively determining venous pressure and using the venous pressure as reference for determining and/or validating the pressure gradient. For these embodiments of the exemplary method, the blood flow velocity measurements may be achieved through magnetic resistance imaging. Additionally or alternatively, the aortic pressure may be obtained through blood pressure cuff measurements.

In at least one exemplary embodiment of a method for noninvasively determining one or more cardiac pressure measurements, the method comprises the steps of (a) generating a patient-specific medical image of at least one portion of a heart noninvasively through magnetic resonance imaging or external ultrasound; (b) obtaining at least one measurement related to the position of the left ventricular free wall and the interventricular septum from the patient-specific medical image; (c) determining at least a free vibration measurement from a free wall of a left ventricle of the heart in the patient-specific medical image; (d) determining end-diastolic Young's modulus of the left ventricular free wall using the free vibration measurement; (e) determining patient-specific material parameters of the heart in diastolic strain energy function through numerical optimization (inverse method) such that a Young's modulus value from strain energy function is derived that is substantially equal to the value of the end-diastolic Young's modulus of the left ventricular free wall determined from the free vibration measurement; (f) determining the left ventricular end-diastolic pressure by iterative solution such that a predicted left ventricular free wall position substantially matches the measurements related to the left ventricular free wall position; and (g) determining right ventricular end-diastolic pressure by iterative solution such that a predicted end-diastolic interventricular septum position substantially matches the measurements related to the position of the interventricular septum.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

An overview of the features, functions and/or steps of the methods depicted in the various figures will now be presented. It should be appreciated that not all of the steps and/or features of the methods depicted in the figures are necessarily expressly described herein; rather, certain non-discussed steps and/or features, such as various instruments and/or apparatus for measurement, computer processors for computing some or all of the calculations disclosed herein, etc., are inherent from the figures and disclosure itself.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

At least one objective of the disclosure of the present application is to introduce new methods to determine LVEDP, RV and pulmonary pressures based on solid theoretical grounds. For the purpose of promoting understanding, the steps of the methods disclosed herein will first be generally described, followed by a more detailed description of the relevant computations associated with the various steps of the method embodiments.

Figure 1:
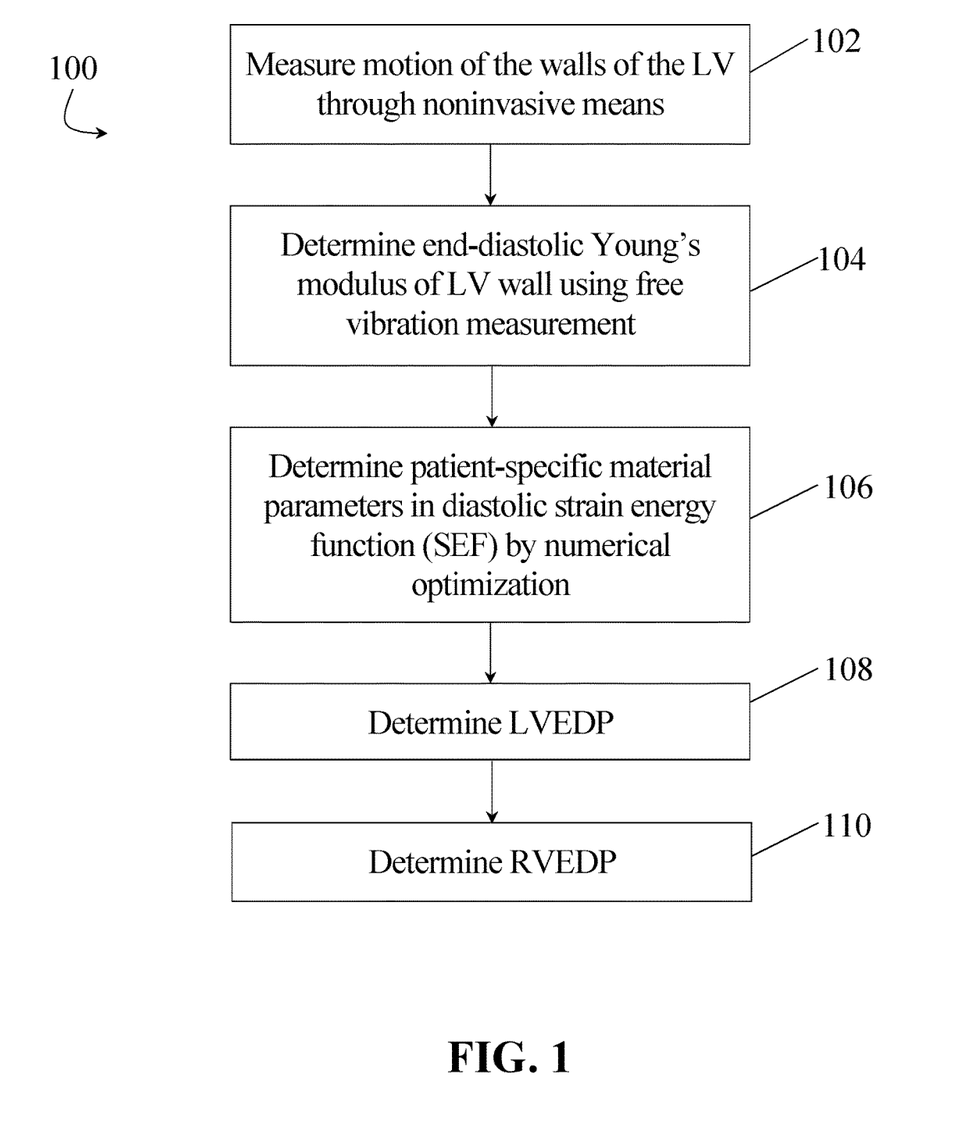
FIG. 1 shows a flow chart of a method for noninvasively determining various pressures, according to an exemplary embodiment of the present disclosure.

FIG. 1 shows a flow chart of at least one embodiment of a method 100 for noninvasively determining heart and/or pulmonary pressures in accordance with an exemplary embodiment of the present disclosure. For example, in at least one embodiment, method 100 may be employed to noninvasively determine the LVEDP of a heart. Alternatively or additionally, embodiments of method 100 may be performed to noninvasively determine right ventricular end-diastolic pressure (RVEDP).

The LV of a heart comprises an elastic, spherical shell formed in part by the LV free wall. The LV free wall is composed of the area of the LV wall that is not in contact with the interventricular septum and that is not part of the LV apex. At step 102 of the method 100, the motion of the walls of the LV is measured through noninvasive means. For example, in at least one embodiment, the free vibrations of the LV free wall and interventricular septum are recorded through the use of patient-specific imaging such as magnetic resonance imaging (MRI) and/or echocardiography. Such measurements taken at step 102 can also include identifying the LV internal radius and the LV wall thickness (which are used in determining free wall vibration), as well as any other information and/or measurements from the patient-specific image that are relevant to the positions of the heart walls and interventricular septum. At step 104, the end-diastolic Young's modulus of the LV free wall of the heart is determined based on the measurements obtained in step 102 pursuant to the equations detail below.

At step 106, patient-specific material parameters in diastolic strain energy function (SEF) are determined. Specifically, numerical optimization (inverse method) is employed such that Young's modulus from SEF equals to that from free vibration measured in step 102. The value of the LVEDP (minus intrapericardial pressure) is determined at step 108 by iterative solution such that the predicted LV end-diastolic free wall position matches the noninvasive measurements from step 102. At step 110, the value of LVEDP minus RV end-diastolic pressure (RVEDP) can be determined by matching predicted interventricular septum position to the noninvasive measurements determined at step 102. Accordingly, method 100 provides a technique through which accurate LVEDP and/or RVEDP measurements may be achieved through noninvasive means.

Figure 2:
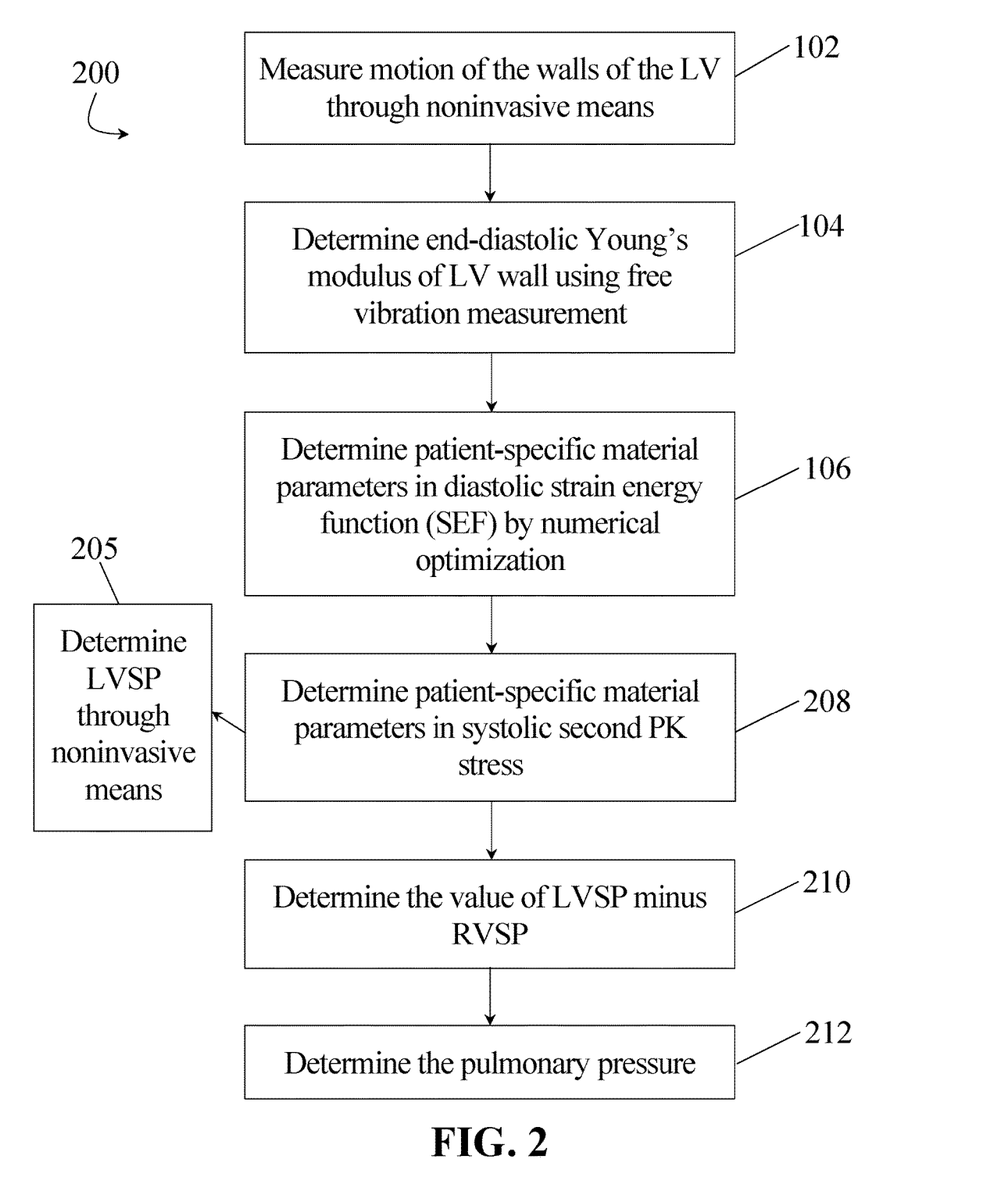
FIG. 2 shows a flow chart of a method for noninvasively determining right ventricular systolic pressure and/or pulmonary pressure according to an exemplary embodiment of the present disclosure.

Now referring to FIG. 2, a flow chart of at least one embodiment of a method 200 for noninvasively determining the RV systolic pressure (RVSP) within a heart is shown. For determination of RVSP in accordance with an exemplary embodiment of the present disclosure, the method 200 proceeds through steps 102, 104, and 106 as previously described in connection with method 100. Additionally, method 200 further comprises step 205. At step 205 the LV systolic pressure (LVSP) is determined through noninvasive means. As previously noted, LVSP ($P_{LVSP}$) equals the synchronous aortic pressure (i.e., $P_{LVSP}=P_{AP}$) and can therefore be accurately determined in a noninvasive manner. Thereafter, in at least one embodiment of the method 200, steps 106 and 205 advance to step 208. At step 208, patient-specific material parameters in systolic second Piola-Kirchhoff (PK) stress are calculated by numerical optimization (inverse method) such that the predicted LV systolic free wall position matches the non-invasive measurements taken at step 102. In conjunction with LVSP and intrapericardial pressure, at step 210 the value of LVSP minus RVSP is determined by iterative solution such that the predicted systolic interventricular septum position matches non-invasive measurements determined at step 102. Furthermore, at step 212, pulmonary pressure can be determined by subtracting the pressure gradient estimated from flow measurements from the calculated RVSP value.

Figure 3:
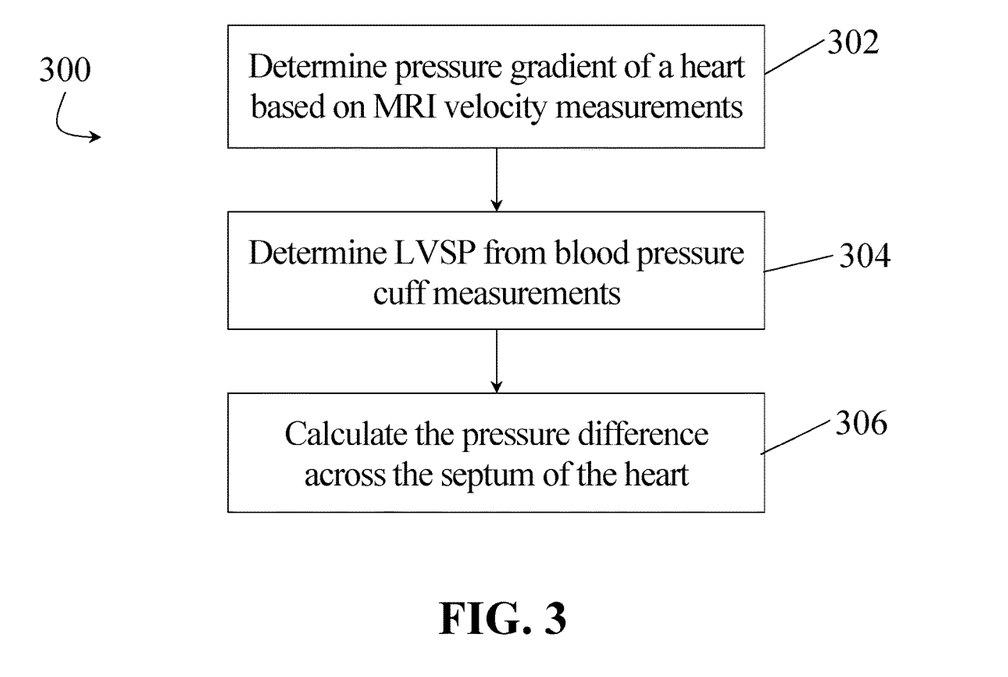
FIG. 3 shows a flow chart of a method for the noninvasive determination of right ventricular systolic pressure according to an exemplary embodiment of the present disclosure.

FIG. 3 illustrates at least one additional embodiment of a method 300 for the noninvasive determination of the RVSP of a heart which includes: 1) determining at step 302 the pressure gradient (from Navier Stokes equation) based on MRI velocity measurements in the RV of a patient, 2) determining at step 304 the LVSP from such patient's blood pressure cuff measurements, and 3) calculating at step 306 the pressure difference ($LVSP_{septum}-RVSP_{septum}$) across the septum. The LVSP and RVSP are coupled through the mechanics of the septum, the stress which can be computed as outlined below and the strain of which can be directly measured from MRI tagging. Hence, the determination of $RVSP_{septum}$ in conjunction with pressure gradient in the RV provides the absolute systolic pressure measurements in the RV.

It will be appreciated that methods 100, 200 and/or 300 may be performed independently or in conjunction with each other depending on which pressures are desired. For example, in at least one exemplary embodiment, methods 100 and 200 are performed together such that steps 102, 104 and 106, which overlap between the two methods 100, 200 need only be performed once. Additionally or alternatively, methods 100 and 300 may be performed together to determine LVEDP, RVEDP, LVSP and RVSP measurements.

As generally discussed in connection with the steps of the methods 100, 200, and 300, the specific computations relating to the appropriate steps of such methods will now be described. If the LV wall vibration at the end-diastole is approximated by the free vibration of an elastic shell, the end-diastolic Young's modulus of LV free wall (E) can be determined at step 104 as follows:

$$E = \rho \left[ \frac{rf}{A\left(\frac{h}{r}\right)} \right]^2 \quad [1]$$

where $\rho$ is the myocardial density ($1.02\times10^3$ kg/m$^3$), r the LV internal radius, h the LV wall thickness, $$A\left(\frac{h}{r}\right)$$

is a function of $$\frac{h}{r}$$

and is independent of elasticity. The LV instantaneous mode-2 eigenfrequency, f, may be determined by MRI, echocardiography or other noninvasive imaging technology.

The diastolic myocardial mechanics (e.g., evaluated in step 106) may be described by the strain energy function (which is transversely isotropic with respect to the local muscle fiber direction) as:

$$W = \frac{C_d}{2}\left\{\exp\left[\begin{array}{l}b_f E_{11}^2 + b_t(E_{22}^2 + E_{33}^2 + E_{23}^2 + E_{32}^2) + \\ b_{fs}(E_{12}^2 + E_{21}^2 + E_{13}^2 + E_{31}^2)\end{array}\right] - 1\right\} \quad [2]$$

where $c_d$, $b_f$, $b_t$ and $b_{fs}$ are diastolic myocardial material parameters, $E_{11}$ is the fiber strain, $E_{22}$ is cross-fiber in plane strain, $E_{33}$ is radial strain, and the rest are shear strains. Furthermore, the corresponding second Piola-Kirchhoff stress (S) can be derived through:

$$S_{diastole} = pJC^{-1} + 2J^{-\frac{2}{3}}Dev\left(\frac{\partial \tilde{W}}{\partial \tilde{C}}\right) \quad (3)$$

where p is the hydrostatic pressure introduced as the Lagrange multiplier needed to enforce incompressibility, J is the Jacobian of the deformation gradient tensor, C is the right Cauchy-Green deformation tensor and Dev is the deviatoric projection operator. Cardiac myofiber can be assigned at the epicardium, midwall and endocardium, based on MRI measurments. Material parameters ($b_f$, $b_t$, $b_{fs}$, and stiffness parameter, $c_d$) may be determined by numerical optimization (inverse method)[11] such that the Young's modulus of LV free wall from Eqs. [2] and [3] equals to that from Eq. [1].

Furthermore, the value of LVEDP minus intrapericardial pressure can be determined by iterative numerical solution (e.g., in step 108 of method 100) such that the predicted LV end-diastolic free wall position matches the measurements obtained by MRI, echocardiography or other noninvasive imaging technique when intrapericardial pressure equals to previous measurements. Similarly, the value of LVEDP minus RVEDP can be determined by iterative numerical solution such that the predicted interventricular septum position matches the measurements from MRI, echocardiography or other imaging report with computed LVEDP (step 110 of method 100).

Systolic second Piola-Kirchhoff stress can be derived from the sum of the diastolic stress and an active fiber directional component, $T_0$, through:

$$S_{systole} = S_{diastole} + T_0 \quad [4]$$

$$T_0 = \frac{1}{2} T_{max} \frac{Ca_0^2}{Ca_0^2 + ECa_{50}^2} \left[1 - \cos\left(\frac{0.25}{1.0489 \cdot 1.85 \cdot \sqrt{2E_{11}+1}+b} + 1\right)\pi\right] \quad [5]$$

$$ECa_{50} = \frac{(Ca_0)_{max}}{\sqrt{\exp[4.75(1.85\sqrt{2E_{11}+1} - 1.58)] - 1}} \quad [6]$$

where $c\alpha_0$ is the peak intracellular calcium concentration (subscript$_{max}$ represents maximum) and $T_{max}$ represents the maximal strength of contraction. In accordance with biaxial data, cross-fiber, in-plane stress equivalent to about 40% of that along the myocardial fiber direction is added. Patient-specific material parameter $T_{max}$, $c\alpha_0$, and $(c\alpha_0)_{max}$ may be determined (e.g., at step 208 of method 200) by matching the predicted LV systolic free wall position to the measurements from MRI or echocardiography or other noninvasive imaging when $P_{LVSP}=P_{AP}$ and the intrapericardial pressure is equal to previous measurements. The value of LVSP minus RVSP can be determined by numerical solution such that the predicted interventricular septum position matches the measurements from MRI, echocardiography or any other noninvasive imaging technique. As such, the computations thereafter allow for the straightforward calculation of RVSP (step 210 of method 200). Finally, pulmonary pressure may be determined (e.g., at step 212 of method 200) from RVSP and pressure gradient determined from MRI velocity measurements.

Additionally or alternatively, venous pressure can be measured noninvasively and used to supplement the equations described herein and/or reference certain pressure difference measurements determined in connection with performance of methods 100, 200 and/or 300. For example, venous pressure can be measured noninvasively by gradually occluding a vein with a cuff applied to an arm or leg of a patient and visualizing the relevant vein with ultrasound or other appropriate imaging techniques until the cuff pressure collapses the vein. At the point of vein collapse, the cuff pressure equals the vein pressure.

Because the right atrium of a heart is connected to the venous system, an absolute venous pressure measurement determined as described above can be used as an accurate reference for any pressure difference measurements made for the right atrium (i.e. central venous pressure). Additionally, when blood flows from the right atrium of the heart to the right ventricle through the open tricuspid valve during diastole, the right atrium and right ventricle experience the same pressures. Furthermore, the right ventricle is connected to the pulmonary artery (PA) which has the same pressure as the right ventricle in systole when the PA valve is open. Accordingly, a clinician may easily obtain an accurate measurement of a patient's venous pressure through noninvasive means and subsequently include such data in the evaluation of the pressures of a heart according to the methods described herein.

Amy number of the method steps and/or operations referenced herein can be performed using a computer, such as a processor in communication with a storage medium, the storage medium configured to store data, and wherein the processor can processor obtained data (such as measurement data) to perform the computations referenced herein.

While various embodiments of methods for non-invasive determination of heart and pulmonary pressures have been described in considerable detail herein, the embodiments are merely offered as non-limiting examples. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method for noninvasively determining one or more pressure measurements comprising the steps of:
   generating a patient-specific medical image of at least one portion of a heart of a patient noninvasively;
   determining, from the medical image, a measured position of a left ventricular free wall of the heart;
   determining from the patient-specific medical image at least two measurements from a portion of the heart, one of the at least two measurements comprising a free vibration measurement determined from the left ventricular free wall of the heart shown in the medical image, and one of the at least two measurements relating to the measured position of the left ventricular free wall;
   calculating at least one targeted pressure within one or more portions of at least one of the heart and an adjacent vessel using one or more computations and at least one of the at least two measurements, the at least one targeted pressure comprising a first targeted pressure comprising a left ventricular end-diastolic pressure and at least one of the one or more computations for determining the left ventricular end-diastolic pressure by iterative solution that numerically optimizes a calculated position of the left ventricular free wall to match the measured position of the left ventricular free wall;
   calculating a blood flow velocity and determining a pressure gradient from the blood flow velocity, the pressure gradient determined from magnetic resonance imaging blood flow velocity measurements through a right ventricle of the heart;
   noninvasively determining venous pressure; and
   using the venous pressure as reference for at least one of determining and validating the pressure gradient;

wherein at least one of the one or more computations determines an end-diastolic Young's modulus value of the left ventricular free wall using the free vibration measurement;

wherein at least one of the one or more computations determines patient-specific material parameters in diastolic strain energy function of the heart, where through numerical optimization a Young's modulus value from strain energy function equals the value of the end-diastolic Young's modulus value of the left ventricular free wall; and wherein the preceeding steps are performed using a computer, the computer comprising a processor capable of processing obtained data.

2. The method of claim 1, wherein the targeted pressure is selected from the group consisting of a left ventricle end-diastolic pressure, a right ventricle pressure, and a pulmonary pressure.

3. The method of claim 1, wherein the patient-specific medical image of at least a portion of the heart is generated through magnetic resonance imaging or echocardiography.

4. The method of claim 1, wherein:
at least one of the at least one measurement determined from the patient-specific medical image relates to the position of the interventricular septum; and
at least one of the computations used in the calculating at least one targeted pressure determines right ventricular end-diastolic pressure by iterative solution such that a predicted end-diastolic interventricular septum position matches the at least one measurement related to the position of the interventricular septum.

5. The method of claim 1, wherein determining a pressure gradient further comprises calculating the pressure gradient using a Navier-Stokes equation.

6. The method of claim 1, further comprising the step of determining left ventricular systolic pressure by noninvasively measuring aortic pressure; left ventricular systolic pressure being at aortic pressure.

7. The method of claim 6, further comprising:
determining, from the medical image, a position of a left ventricle systolic free wall of the heart, wherein:
at least one of the at least two measurements determined from the patient-specific medical image relates to the position of the left ventricle systolic free wall;
at least one of the at least one targeted pressure comprises a third targeted pressure comprising right ventricular systolic pressure; and
at least one of the one or more computations used in the calculating the third targeted pressure determines patient-specific material parameters of the heart using a systolic second Piola-Kirchhoff stress value and numerical optimization such that a predicted left ventricle systolic free wall position equates with the at least one measurement related to the position of the left ventricle systolic free wall.

8. The method of claim 7, further comprising determining, from the medical image, a position of a systolic interventricular septum of the heart, wherein:
at least one of the at least two measurements determined from the patient-specific medical image relates to the position of a systolic interventricular septum; and
at least one of the one or more computations used in the calculating the at least one targeted pressure determines right ventricular systolic pressure by iterative solution such that a calculated systolic interventricular septum position matches the at least one measurement related to the position of the systolic interventricular septum.

9. The method of claim 8, further comprising the step of calculating a fourth targeted pressure within one or more portions of at least one of the heart and an adjacent vessel, wherein the third targeted pressure comprises pulmonary pressure derived from the right ventricular systolic pressure and the pressure gradient.

10. The method of claim 6, further comprising the steps of:
assessing a pressure difference across an interventricular septum of the heart in view of the left ventricular systolic pressure to determine right ventricular systolic pressure.

11. The method of claim 10, wherein the aortic pressure is obtained through blood pressure cuff measurements.

12. The method of claim 1, further comprising the step of:
calculating a second targeted pressure of the at least one targeted pressure within one or more portions of at least one of the heart and an adjacent vessel using at least one of the one or more computations and at least one of the at least two measurements.

13. The method of claim 12, wherein the second targeted pressure comprises left ventricular systolic pressure and the step of calculating the second targeted pressure comprises calculating left ventricular systolic pressure by noninvasively measuring aortic pressure of the patient, wherein left ventricular systolic pressure is at aortic pressure.

14. A method for noninvasively determining one or more pressure measurements comprising the steps of:
generating a patient-specific medical image of at least one portion of a heart of a patient noninvasively;
determining, from the medical image, a first free vibration measurement from a left ventricle systolic free wall of the heart;
determining, from the medical image, a position of the left ventricle systolic free wall of the heart and a position of a systolic interventricular septum of the heart;
determining a second free vibration measurement related to the position of the systolic interventricular septum from the medical image;
calculating left ventricular systolic pressure by noninvasively measuring aortic pressure of the patient, wherein left ventricular systolic pressure is at aortic pressure;
calculating a blood flow velocity and determining a pressure gradient from the blood flow velocity, the pressure gradient determined from magnetic resonance imaging blood flow velocity measurements through a right ventricle of the heart;
calculating an end-diastolic Young's modulus value of the left ventricular free wall using the second free vibration measurement;
determining a first patient-specific material parameter of the heart in diastolic strain energy function using a first numerical optimization such that a Young's modulus value from strain energy function matches the end-diastolic Young's modulus value of the left ventricular free wall;
determining a second patient-specific material parameter of the heart using a systolic second Piola-Kirchhoff stress value and a second numerical optimization such that a left ventricle systolic free wall position matches the position of the left ventricle systolic free wall of the heart determined from the medical image;
determining a right ventricular systolic pressure by iterative solution such that a predicted systolic interventricular septum position matches the position of the systolic interventricular septum determined from the medical image;

noninvasively determining venous pressure;
using the venous pressure as reference for validating the pressure gradient; and
wherein the preceeding steps are performed using a computer, the computer comprising a processor capable of processing obtained data.

\* \* \* \* \*